United States Patent [19]

Brown et al.

[11] Patent Number: 5,439,102
[45] Date of Patent: Aug. 8, 1995

[54] PACKAGE FOR SURGICAL SUTURES

[75] Inventors: David L. Brown, Wallington; Stanley J. Malinowski, Ridgefield; J. Larry Hineline, Fairfield, all of Conn.

[73] Assignee: United States Surgical Corporation, Norwalk, Conn.

[21] Appl. No.: 171,202

[22] Filed: Dec. 21, 1993

Related U.S. Application Data

[63] Continuation of Ser. No. 911,287, Jul. 9, 1992, abandoned.

[51] Int. Cl.6 .............................................. A61B 17/06
[52] U.S. Cl. .................... 206/63.3; 206/227; 53/397; 383/205
[58] Field of Search ............... 206/63.3, 227, 484, 206/436, 210; 383/66, 205; 53/397

[56] References Cited

U.S. PATENT DOCUMENTS

| | | |
|---|---|---|
| 3,189,174 | 6/1965 | Cormack ............... 206/63.3 |
| 3,221,873 | 12/1965 | Bowes et al. . |
| 3,545,608 | 12/1970 | Berger et al. . |
| 3,648,949 | 3/1972 | Berger et al. . |
| 3,685,720 | 8/1972 | Brady ................... 206/438 X |
| 3,749,238 | 7/1973 | Taylor . |
| 3,754,700 | 8/1973 | Bonk . |
| 3,939,969 | 2/1976 | Miller et al. . |
| 3,972,418 | 8/1976 | Schuler et al. . |
| 4,192,420 | 3/1980 | Worrell, Sr. et al. . |
| 4,352,429 | 10/1982 | Newman . |
| 4,369,880 | 1/1983 | Giggey et al. . |
| 4,412,614 | 11/1983 | Ivanov et al. . |
| 4,494,653 | 1/1985 | Praderio ............... 206/210 X |
| 4,574,948 | 3/1986 | Huck et al. . |
| 4,961,498 | 10/1990 | Kalinski et al. . |
| 5,222,978 | 6/1993 | Kaplan et al. ......... 206/63.3 X |
| 5,246,104 | 9/1993 | Brown et al. ............ 206/63.3 |

FOREIGN PATENT DOCUMENTS

| | | |
|---|---|---|
| 0471441 | 2/1992 | European Pat. Off. . |
| 0494081 | 7/1992 | European Pat. Off. . |
| 4020089 | 6/1991 | Germany . |
| 2132162 | 7/1984 | United Kingdom . |

Primary Examiner—Bryon P. Gehman

[57] ABSTRACT

A moisture impervious package for surgical elements such as retainers having suture-needle assemblies positioned thereon. The package is provided with a top wall of moisture impervious material having an access opening die cut into the wall over which a closure flap secured by a peripheral heat seal to fully enclose the access opening. The top wall is then positioned over a bottom wall of moisture impervious material whereby a retainer having the suture needle assemblies is positioned therebetween. A peripheral heat seal then secures the top wall to the bottom wall to form the package.

32 Claims, 5 Drawing Sheets

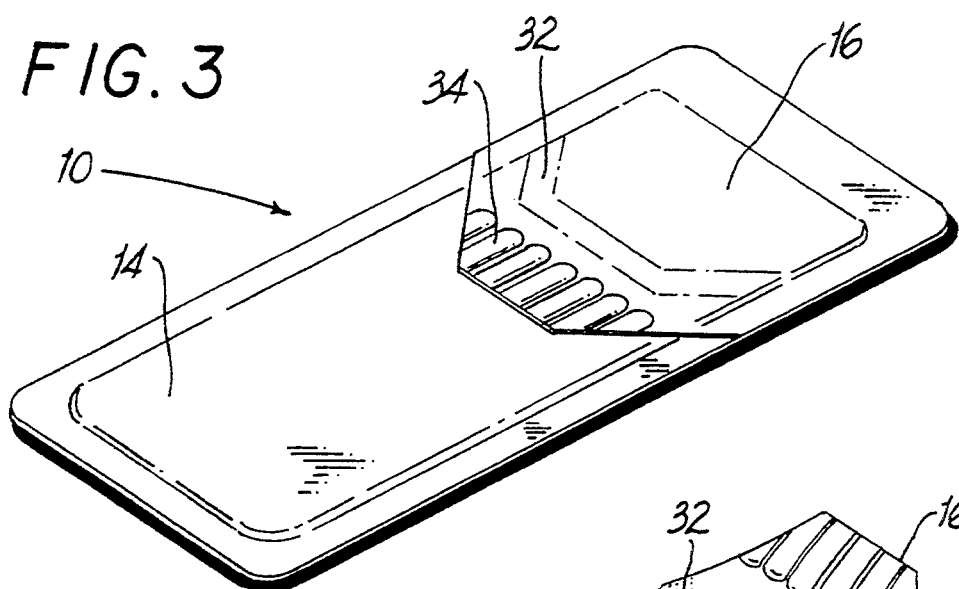
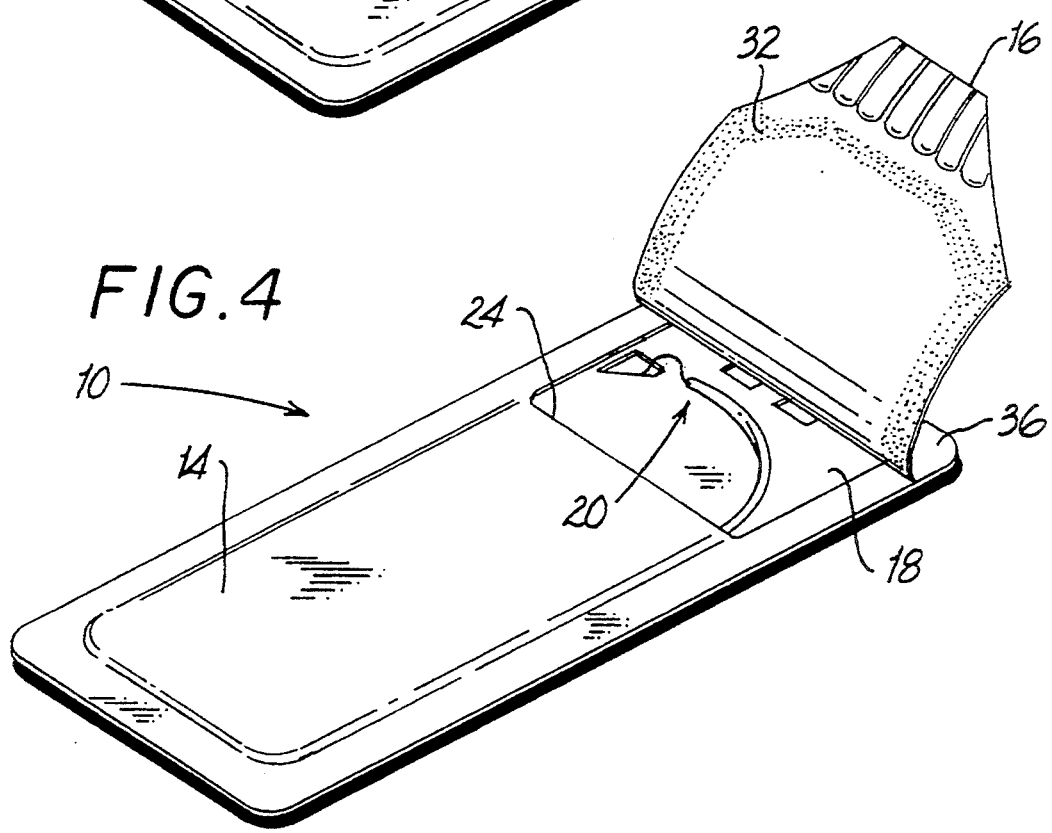
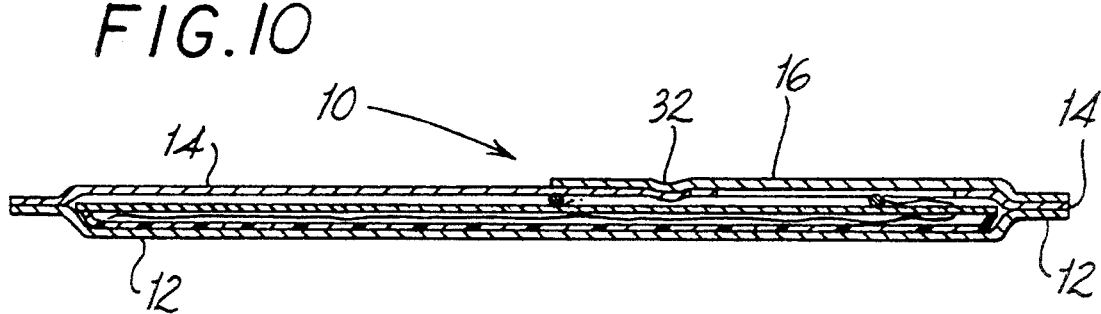

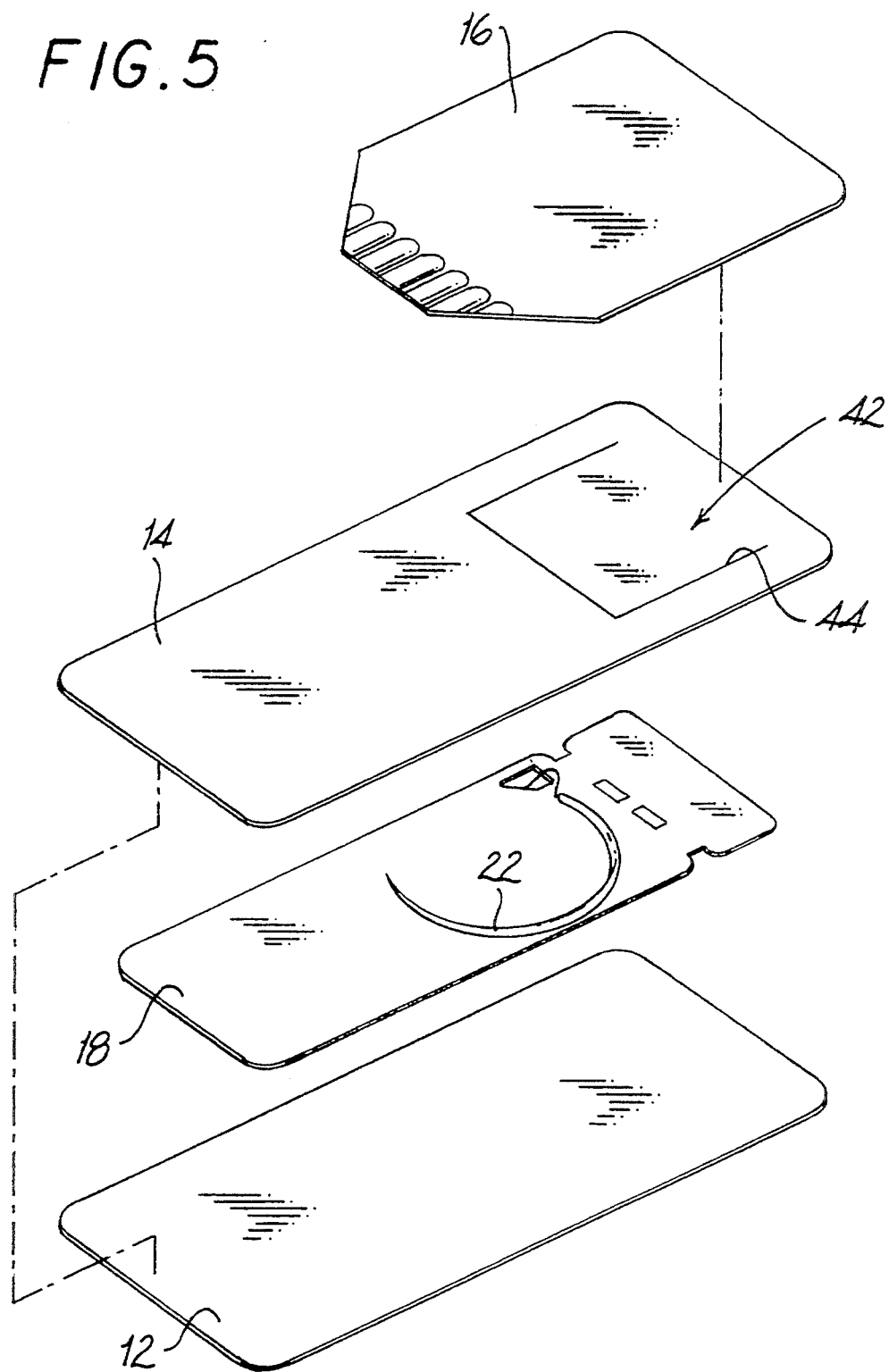

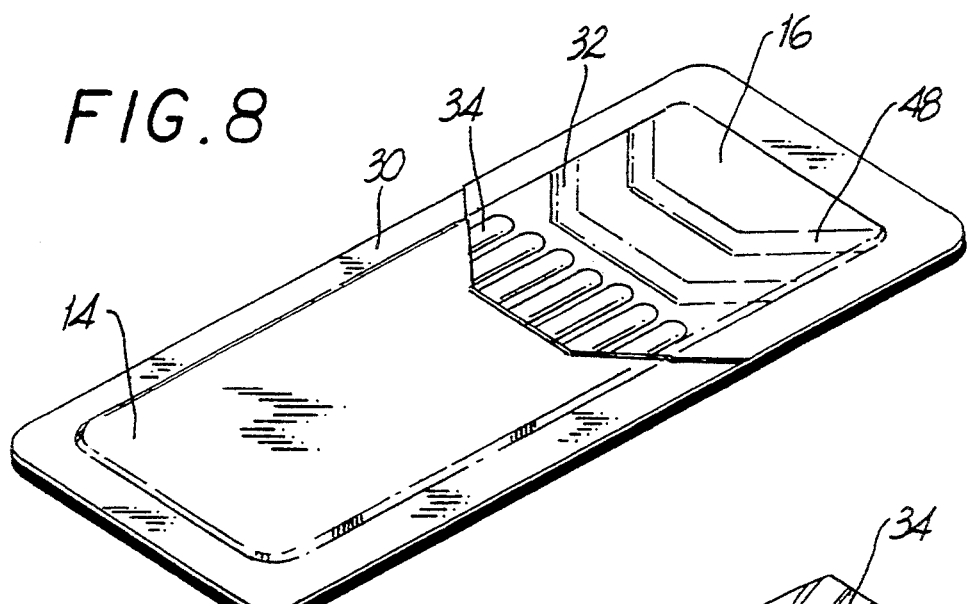
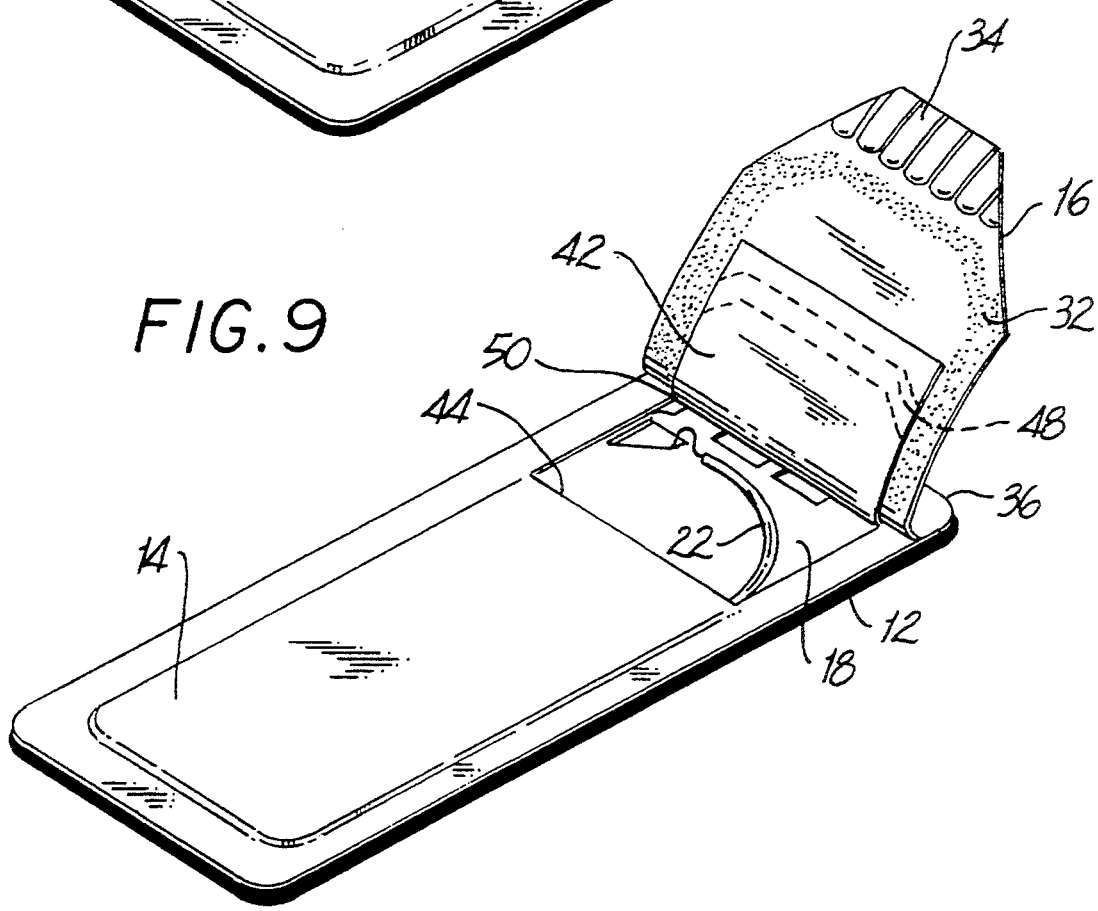
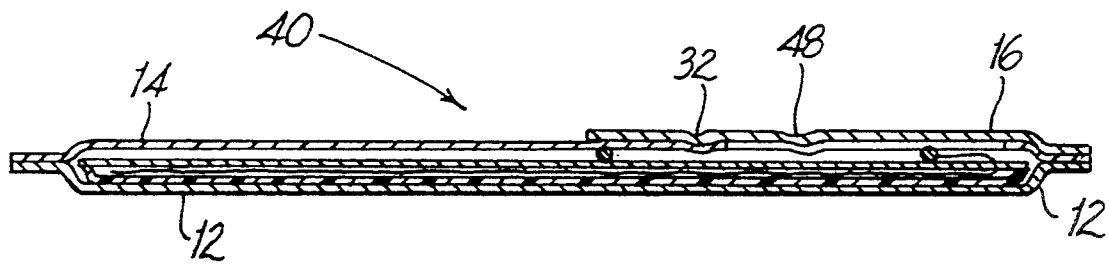

PACKAGE FOR SURGICAL SUTURES

This is a continuation of application Ser. No. 07/911,287 filed on Jul. 9, 1992, now abandoned.

BACKGROUND OF THE INVENTION

1. Field of the Invention

The present invention relates to packages for surgical instruments and devices, and more particularly to moisture impervious packages for surgical devices such as suture-needle assemblies which may be packed in a conditioning fluid medium.

2. Discussion of the Prior Art

Packages constructed of moisture impervious materials for surgical instruments and elements, such as surgical suture-needles and sutures in general, are well known in the art. These packages generally include a retaining member for holding the surgical elements in place within the package. The retainer is completely enclosed and sealed within the package to maintain sterility and prevent contamination of the surgical elements.

Packages constructed of moisture impervious material for surgical elements such as sutures and suture-needle assemblies are generally sealed by means of a heat seal device which creates a peripheral heat seal about the outer edges of the package. The material of which these packages are constructed usually include metal foil such as aluminum backed in laminate form with a plastic material such that the plastic forms the interior surface of the package.

The package is generally formed from a first wall of material upon which the retaining device holding the sutures or suture-needle assemblies is placed. A second wall then overlays the retainer and first wall of material, and a weld seal is formed by applying heat and pressure about the peripheral edge to completely seal the package and form the pocket therebetween which houses the retainer and sutures. This construction however, makes opening the package difficult and handling of the sutures inconvenient since the package typically must be torn open to access the contents.

In an improved form of package the second wall may cover only a portion of the retainer and first wall, and a closure flap member is then positioned to cover the remainder of the retaining device and first wall, and to overlap the second wall. The flat heat seal is then formed about the periphery of the package to seal the first wall to the second wall and the closure flap, as well as to seal the closure flap to the second wall to completely seal the package. In this construction an adhesive layer is provided between the closure flap and the first and second walls so that the package may be peeled open without tearing, by pulling the closure flap. This "mid-peel" construction facilitates opening of the package and makes handling of the sutures easier.

Many sutures and suture-needle assemblies require moisture impervious packaging to prevent evaporation of the conditioning fluid medium in which these elements are packaged. For example, sutures constructed of a gut-type material or a collagen material typically are packaged in a conditioning medium such as alcohol to prevent the sutures from drying out and cracking. In order to eliminate the possibility of evaporation of the alcohol medium, moisture impervious packages are provided to seal the alcohol therein and prevent leakage. To this end, the heat seal which is formed about the periphery of the package must also be impervious to moisture and not be susceptible to cracking in order to prevent the leakage and evaporation of the alcohol medium.

The mid-peel package with the peelable closure flap provides distinct advantages over the conventional tearable foil packages and is preferred. Depending on how the manufacturing and assembly process is conducted, however, it has been found that the presence of an alcohol conditioning fluid may cause difficulties in assembling the package so that the package seal is not compromised. By way of example, if the conditioning fluid is added before the closure flap is sealed to either or both of the first or second walls it is possible that alcohol vapor from the conditioning fluid may interfere with or hinder the adhesive curing process. This may cause an inadequate seal, possibly due to microscopic cracks or fissures across the seal area, thereby allowing the alcohol conditioning fluid to leak or evaporate from the package over time, resulting in a stiff suture at the time of use.

The novel packaging device for surgical elements such as sutures and suture-needle assemblies of the present invention obviates the disadvantages encountered in the prior art tearable packages and provides an improved peelable package which substantially eliminates the possibility of leakage of a conditioning fluid medium through the peripheral seal about the edges of the package. Sutures and suture-needle assemblies packaged in the conditioning medium are preserved in the package of the present invention through the provision of a novel arrangement to prevent the leakage and evaporation of the conditioning fluid from the moisture impervious package.

SUMMARY OF THE INVENTION

The present invention provides a novel package for a surgical instrument or element which is constructed of a moisture impervious material and which substantially reduces or eliminates the possibility of leakage of a conditioning fluid medium enclosed in the package through cracks in the peripheral heat seal or separations between the layers which may provide a path from the interior of the package to the external environment.

The package of the present invention provides a first wall of moisture impervious material which overlies a second wall of moisture impervious material having substantially the same dimensions as the first wall to form a pocket therebetween, and further includes a closure flap positioned on the second wall to facilitate opening the package and includes means for accessing the device enclosed therein. A surgical instrument or element, in particular sutures or suture-needle assemblies which may or may not be assembled on a retainer device, are positioned in the pocket between the two walls of material.

In a preferred embodiment of the present invention, the package is provided with a first wall of impervious material over which a second wall having substantially identical dimensions to the first wall lies to form a pocket therebetween. The second wall substantially covers the entire first wall, and the second wall is provided with a cut-out or window in the area of the needles of the suture-needle assemblies. A closure flap member is provided which covers the second wall and overlies the window of the second wall while providing a pull tab for opening the package. The closure flap is first sealed to the second wall to enclose the window, and then the second wall is sealed to the first wall by a continuous heat seal about the periphery of the package to enclose a retainer having suture-needle assemblies therein.

In a second embodiment, the second wall is provided with a die-cut region which may include a series of perforations, a tearable score line, or cut in the material, each of which is preferably in the shape of a "U" to form a tab which is drawn back away from the second wall to access the retainer. In this embodiment, the closure flap includes an additional seal which seals the tab to the closure flap, so that upon removal of the closure flap, the tab is pulled away from the second wall. The package is formed by placing the retainer on the first wall forming the bottom, heat sealing the closure flap to the second wall about its periphery and across its middle to seal the flap to the tab, and then heat sealing the second wall to the first wall about its periphery to enclose the retainer therein.

Many types of sutures, such as gut-type sutures or collagen-type sutures require packaging in a conditioning fluid medium such as alcohol to preserve their suppleness and flexibility. After the sutures and conditioning fluid are positioned between the two walls of material, a peripheral heat seal is applied about the longitudinal edges and the top and bottom transverse edges to form a continuous seal about the package. The heat sealing process tends to accelerate the vaporization of the alcohol, so solidification of the bond between the layers is critical. The seal, being only between the substantially identically dimensioned first and second walls, substantially reduces or prevents evaporation at the heat seal. The provision of the first and second walls having the same shape and dimensions substantially eliminates the possibility of microscopic leaks and cracks forming in the heat seal at the juncture of the closure flap and the second wall to prevent the leakage or evaporation of the conditioning fluid from the interior of the package to the outside environment. Because the first and second walls are not to be peeled apart, the peripheral seal between the first and second walls need not include an adhesive to permit peeling. Rather, the peripheral seal between the first and second walls can be a traditional heat weld seal wherein the polymer inner layer of each wall partially melts and flows together to become a unitary layer. In such a weld seal the polymer layer solidifies as a unitary layer relatively quickly. Peelable bonds including an adhesive layer, on the other hand, require a longer set up time during which vapors from the conditioning fluid can interfere with formation of an effective sealing bond.

The package of the present invention having the closure flap over the window access area possesses several advantages over known packages, particularly during opening of the package. The removal of the closure flap provides access to the suture needles through a one-step opening motion, giving access to the needles without having to regrasp and reposition the package after opening. Less effort is expended during opening, and there is less chance of mishandling the package and sterile suture-needles contained therein during opening. Furthermore, the retainer may be constructed to have a fold-over panel adjacent the needles which is adhesively bonded to the closure flap, or to the die-cut flap, so that opening the closure flap lifts the retainer and exposes the needles while securing the closure flap to the package. In an alternative embodiment, the die cut tab provides added protection to the cover flap in the event the needles shift, in order to prevent puncturing the cover flap. Most importantly, in the present invention the closure flap may be adhered to the second wall before the first and second walls are adhered to one another to form the pocket to receive the surgical suture and conditioning fluid. Thus, the closure flap may first be bonded to the second wall with an adhesive layer therebetween so as to form a peelable seal between the closure flap and second wall. Thereafter, the first and second walls are welded together to form the pocket to receive the suture and conditioning fluid. Because the peelable closure flap is applied to the second wall before the first and second walls are bonded together, and because the first and second walls are weld sealed together without any adhesive layer, the first and second walls may be welded together to form the pocket on line at the same time the suture and conditioning fluid are added to the pocket. In this manner a peelable package manner be provided while advantageously permitting on line formation and loading of the package.

BRIEF DESCRIPTION OF THE DRAWINGS

The foregoing features of the present invention will become more readily apparent and may be understood by referring to the following detailed description of an illustrative embodiment of the package for a surgical suture retainer, taken in conjunction with the accompanying drawings, in which:

FIG. 3 illustrates a perspective view of the package of FIG. 1;

FIG. 4 illustrates a perspective view of the package of FIG. 1 in the opened condition;

FIG. 5 illustrates an exploded perspective view of a second embodiment of the package of the present invention;

FIG. 8 illustrates a perspective view of the package of FIG. 5;

FIG. 9 illustrates a perspective view of the package of FIG. 5 in the opened condition;

FIG. 10 illustrates a side cross sectional view of the package of FIG. 1; and

FIG. 11 illustrates a side cross sectional view of the package of FIG. 5.

DETAILED DESCRIPTION OF THE PREFERRED EMBODIMENTS

Figure 1:
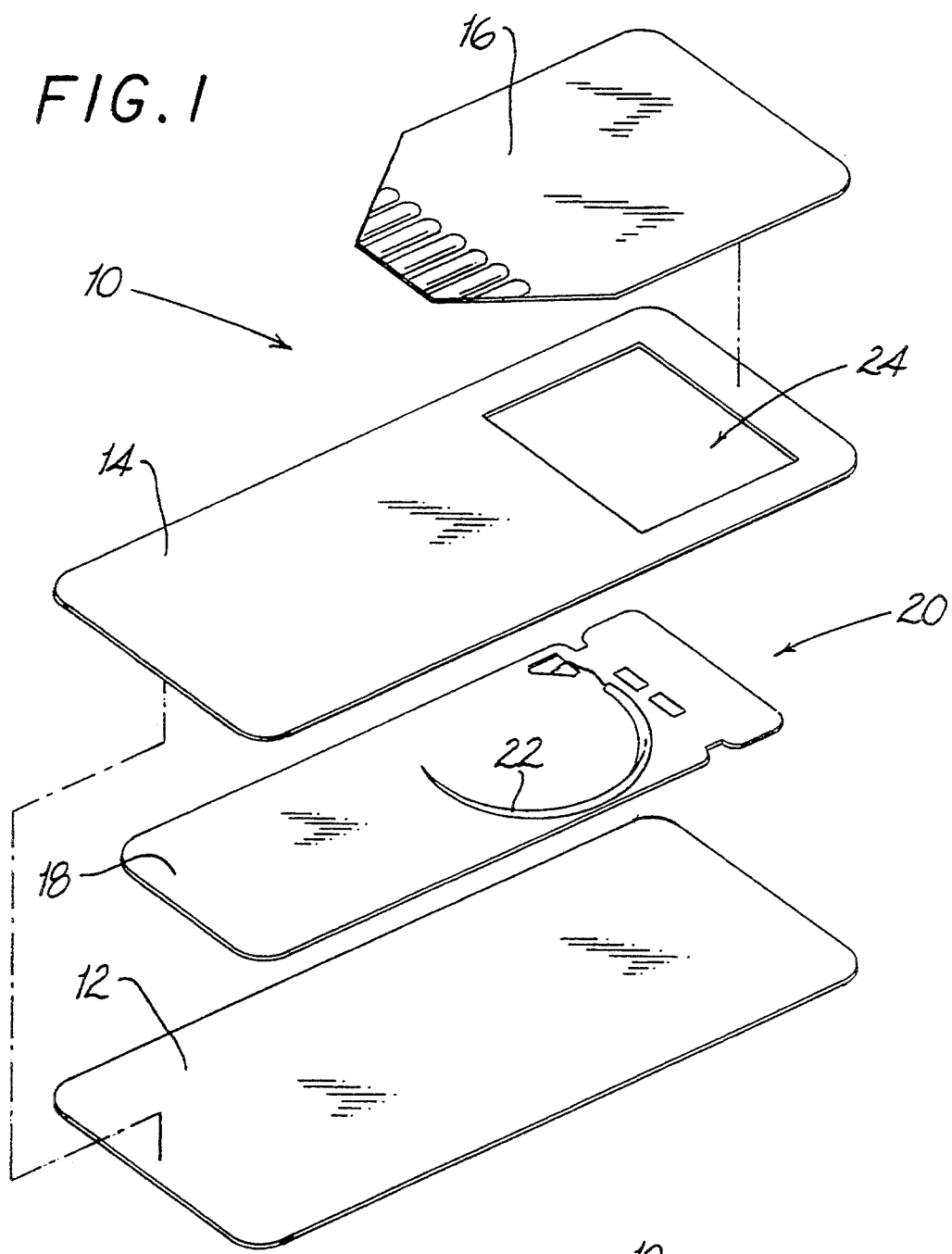
FIG. 1 illustrates an exploded perspective view of a first embodiment of the package of the present invention.

Referring now in specific detail to the drawings, in which like reference numerals identify similar or identical elements throughout the several views, FIG. 1 illustrates an exploded view of the package of the present invention showing all the elements that make up package 10. Package 10 is constructed of a moisture impervious material such as metal foil such as aluminum or a combination of a metal foil and plastic laminate such as polyolefin which substantially prevents moisture from penetrating from the inside of the package to the external environment. A bottom wall 12 is provided upon which a surgical suture-needle retainer is positioned. Retainer 18 preferably contains a plurality of surgical suture-needle assemblies 20 whereby the needles 22 of the assemblies 20 are positioned at an upper edge of the retainer 18 as shown. A top wall 14 is provided to overlie bottom wall 12 having retainer 18 positioned thereon. A closure flap 16 is provided which covers access means 24, whose function will be described below. Bottom wall 12 and top wall 14 form a pocket to enclose retainer 18 therebetween.

Figure 2:
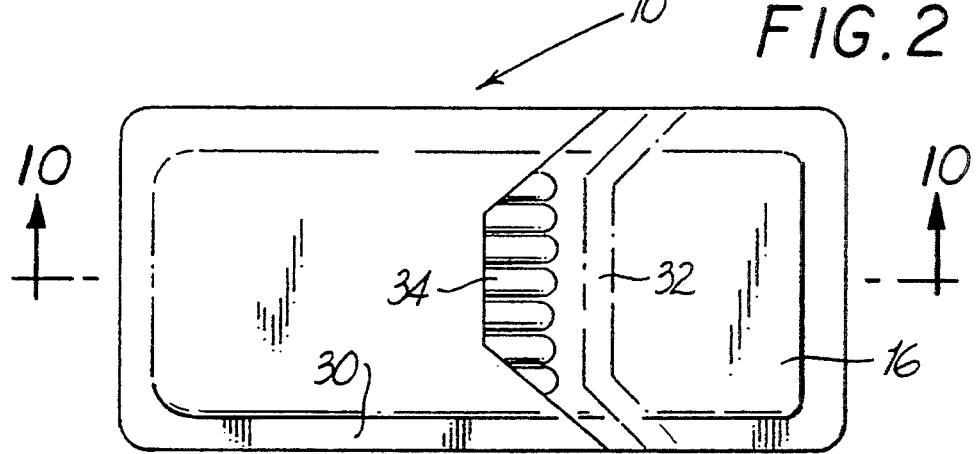
FIG. 2 illustrates a plan view of the package of FIG. 1.

As seen in FIGS. 2 and 3, closure flap 16 is secured to top wall 14 by a peelable peripheral heat seal 32 which encloses and seals access means 24. After retainer 18 is positioned on bottom wall 12, top wall 14, having closure flap 16 attached thereto, is then sealed to bottom wall 12 by peripheral heat weld seal 30. Retainer 18, having suture needles assembly 20 wound thereon, is thereby sealed within moisture impervious package 10 to prevent the evaporation of a conditioning fluid which is applied to the sutures in retainer 18. In all of the embodiments described herein, first and second walls 12, 14 preferably include aluminum foil and polymer layers, and are heat sealed together with the polymer layers in face to face relation so as to form a weld seal therebetween with the polymer layers flowing together to form a unitary layer. The closure flap also includes aluminum foil and polymer layers. In order that the seal between the closure flap and second wall is peelable, however, an adhesive layer is provided between the closure flap and second wall, such as by adding an adhesive heat seal coating layer to the polymer layer on the closure flap. In a preferred construction the first and second wall are a nylon foil laminate, such as 0.6 mil nylon laminated to 2 mil foil. It is contemplated that polyethylene or other polymers may be used instead of nylon on the first and second walls. The peelable closure flap preferably is constructed of 1 mil foil laminated to 1.5 mil high density polyethylene, the polyethylene being coated with RP-1A (Rollprint Packaging, Addison Ill.) heat seal coating at a coating rate of from about 0.02 to about 0.04 ounces per square foot.

Gut-type sutures and other degradable bioabsorbable type sutures require a conditioning fluid to be packaged with the sutures to prevent drying out or cracking. The conditioning fluid is typically an alcohol based fluid medium which maintains the suppleness and flexibility of the sutures within the package. The moisture impervious package is provided to prevent the evaporation of the conditioning fluid, and consequently the destruction of the suture material, and with such a package it is important the package be moisture impervious and that the heat seal which joins the top wall to the bottom wall maintains its integrity throughout the life of the package.

To this end, package 10 of the present invention provides for a continuous heat seal 30 about bottom wall 12 and top wall 14. Closure flap 16 is secured to the top wall 14 by peripheral seal 32 to eliminate the junction between the closure flap, the bottom wall, and the top wall. In use, top wall 14 is formed as having substantially identical dimensions to bottom wall 12, with the addition of a die cut access means 24 being provided in top wall 14. Access means 24 may comprise a window-like opening, which provides access to the retainer 18, and in particular the needles 22, packaged within package 12. Closure flap 16 is first sealed by means of peripheral heat seal 32 to top wall 14 to fully enclose access means 24. Retainer 18 is positioned on bottom wall 12 and top wall 14, having closure flap 16 sealed thereto, is then positioned on bottom wall 12 so that needles 22 lie beneath the region of access means 24. Heat seal 30 is then applied to the periphery of package 10 to enclose retainer 18 within package 10.

As best seen in FIG. 4, a gripping tab 34 is provided on closure flap 16 to allow surgical personnel to grasp flap 16 to open the package 10. As closure flap 16 is pulled away from top wall 12, peelable seal 32 is broken to allow for closure flap 16 to be peeled away from top wall 14. Needles 22 of suture-needle assemblies 20 are positioned within access means 24 to allow suture-needle assemblies 20 to be readily removed from the package through access means 24. Preferably, closure flap 16 remains joined to package 10 at top edge 36.

Figure 6:
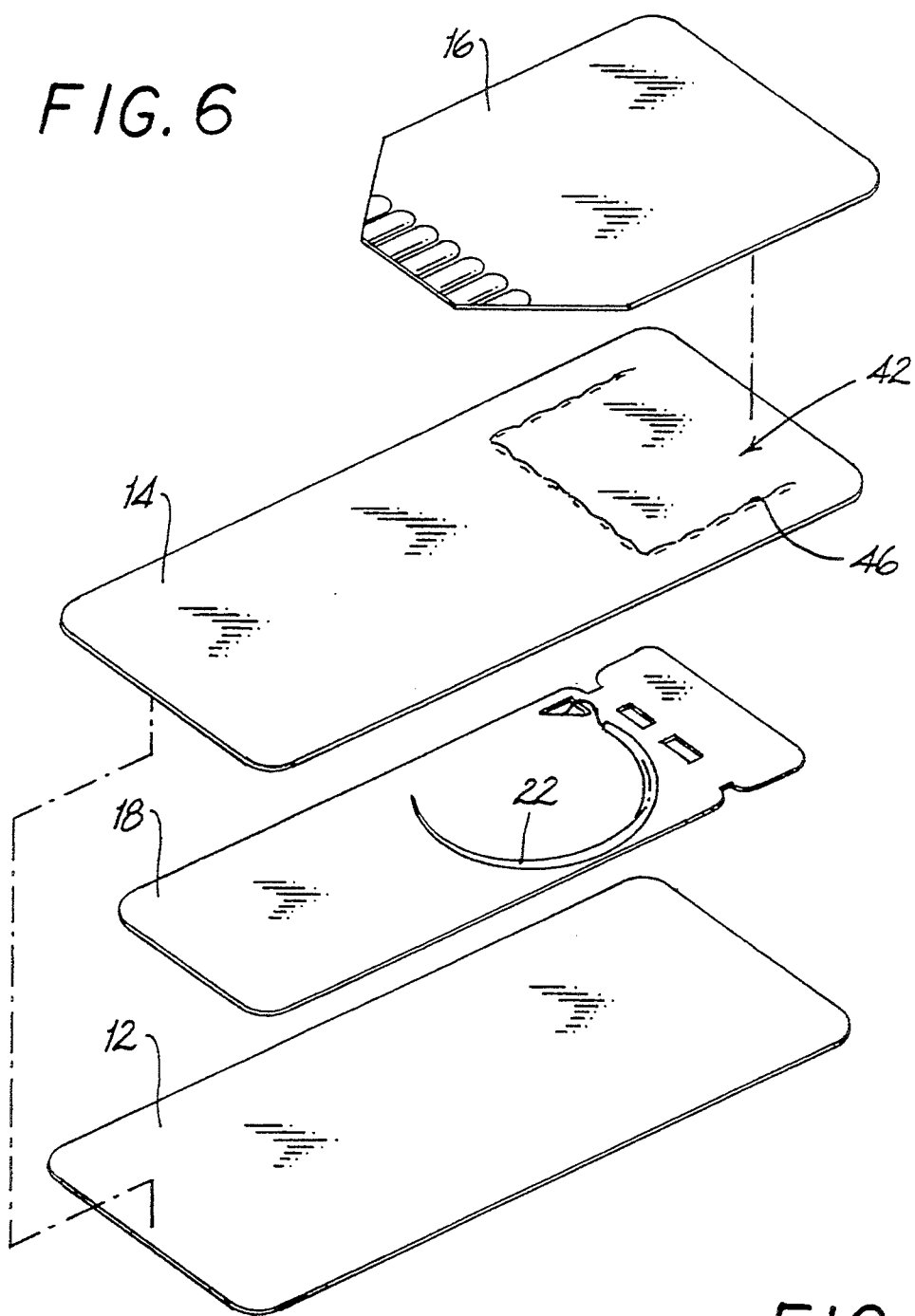
FIG. 6 illustrates an exploded perspective view of a third embodiment of the package of the present invention.

FIGS. 5 and 6 show alternate embodiments of the package of the present invention which are identical to package 10 of FIG. 1 except for the provision of access tab 42 instead of access means 24 of FIG. 1. In FIG. 5, access tab 42 is constructed by applying a U-shaped die cut 44 to top wall 14 which is peelable from top wall 14 in a manner described below. FIG. 6 illustrates access tab 42 as being U-shaped through the provision of perforations 46. While both embodiments show access tab 42 to be U-shaped, it is recognized that die cut 44 or perforations 46 may be continuous so that tab 42 is a removable panel upon opening of the package. In both embodiments, it is contemplated that needles 22 of retainer 18 are positioned beneath access tab 42 so that upon opening of the package the needles are accessible by the surgical personnel.

Figure 7:
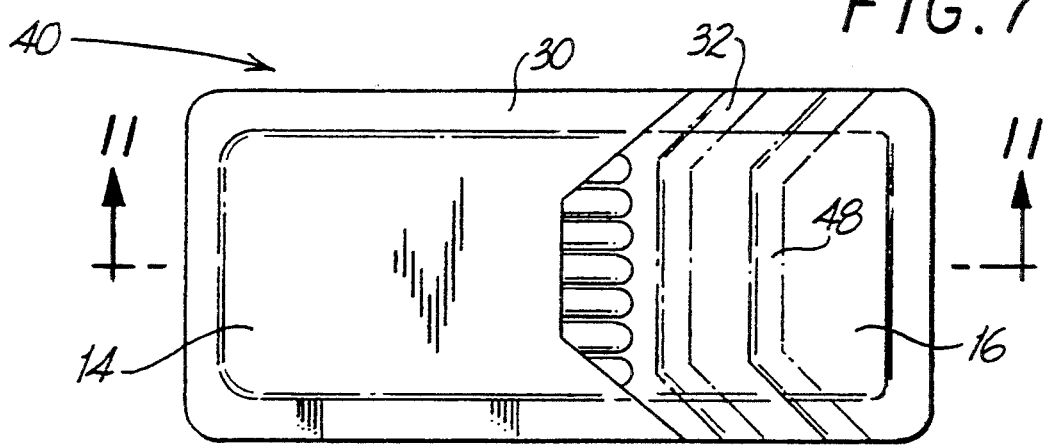
FIG. 7 illustrates a plan view of the package of FIG. 5.

FIGS. 7 and 8 illustrate package 40 which is identical to package 10 except for the further provision of a substantially transverse heat seal 48. As described above in relation to package 10, gripping tab 16 is secured to top wall 14 by peripheral heat seal 32 to fully enclose access tab 42. In this embodiment, however, substantially transverse heat seal 48 is also applied to secure closure flap 16 to top wall 14 across access tab 42 so access tab 42 is secured to closure flap 16. After retainer 18 has been positioned on bottom wall 12, top wall 14 having closure flap 16 secured thereto is positioned on bottom wall 12 so that access tab 42 overlies needles 22. A peripheral heat seal 30 is then applied in the manner described above to secure top wall 14 to bottom wall 12.

As seen in FIG. 9, gripping tab 34 is grasped to pull closure flap 16 away from top wall 14. As peripheral heat seal 32 is broken, access tab 42 is turned upwardly with closure flap 16 due to transverse seal 48 so that access tab 42 is peeled away from top wall 14 to reveal retainer 18 and needles 22 beneath access tab 42. It is preferred that closure flap 16 remains attached to top wall 14 at top edge 36, while access tab 42 remains secured to top wall 14 at edge 50.

As stated above, access tab 42 may be formed by a continuous die cut 44 so that as closure flap 16 is peeled away from top wall 14 as shown in FIG. 9, access tab 42 is completely removed from top wall 14. Closure flap 16 remains secured to top wall 14 at top edge 36.

A further advantage of access tab 42 over an opening such as access means 24 is that in the unlikely event that needles 22 shift in retainer 18, there is added protection against puncture by the needle tips from access tab 42, which reduces the possibility of puncture of closure flap 16.

FIGS. 10 and 11 illustrate side cross-sectional views of the package 10 and 40, respectively, showing the provision in FIG. 10 of peripheral seal 32 and in FIG.

11, showing the additional provision of transverse seal 48.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A package for surgical suture comprising:
   a bottom wall of substantially moisture-impervious material forming a bottom of said package,
   a top wall of substantially moisture-impervious material forming a top of said package, said top wall having substantially the same dimensions as said bottom wall and being positioned in overlying relation on said bottom wall to form a pocket therebetween, said top wall being secured to said bottom wall by a substantially moisture-impervious peripheral seal;
   a surgical suture retainer disposed between said top and bottom walls in said pocket;
   a die-cut portion in one of said walls for accessing at least a portion of said surgical suture retainer therethrough;
   at least one suture associated with said surgical suture retainer, such that at least a portion of said at least one suture is positioned within said die-cut portion; and
   a closure flap of substantially moisture-impervious material overlying at least a portion of said wall from a first end thereof to a position intermediate a second end thereof and sealingly enclosing said die-cut portion along the periphery thereof, said closure flap being secured to said top wall by a substantially moisture-impervious peelable peripheral seal, said closure flap terminating at said intermediate position in a gripping tab portion, whereby said package is opened in a single step by grasping said gripping tab portion and pulling said gripping tab portion from said intermediate position toward said first end.

2. A package according to claim 1, wherein said die-cut tab portion is substantially U-shaped.

3. A package according to claim 2, wherein said closure flap is secured to at least one of said walls by said peripheral seal and at least one substantially transverse seal, said at least one transverse seal securing said closure flap to said U-shaped tab.

4. A package according to claim 3, wherein removal of said closure flap effects opening of said U-shaped tab to access said surgical suture retainer.

5. A package according to claim 1, wherein said moisture-impervious material comprises a laminate.

6. A package according to claim 5, wherein said laminate comprises an outer layer of aluminum and an inner layer of a polyolefin.

7. A package according to claim 1, wherein said moisture-impervious material comprises a metal foil material.

8. A package according to claim 1, wherein said at least one suture is packed in a conditioning fluid medium within said pocket.

9. A package according to claim 1, wherein said at least one suture is packed in an alcohol-based fluid within said pocket.

10. A package for surgical sutures according to claim 1, wherein said at least one suture is bioabsorbable.

11. A package for a surgical suture retainer comprising:
    a first wall of substantially moisture-impervious material;
    a second wall of substantially moisture-impervious material overlying said first wall and having substantially the same dimensions as said first wall, said first and second walls being secured to each other by a substantially moisture-impervious heat seal about a periphery of said first and second walls to form a pocket therebetween receiving a surgical suture retainer;
    a closure flap of substantially moisture-impervious material, said closure flap overlying said second wall from a first end to a position intermediate a second end and secured to said second wall by a peripheral peelable heat seal, said closure flap terminating at said intermediate position in a gripping tab portion, whereby said package is opened in a single step by grasping said gripping tab portion and pulling said gripping tab portion from said intermediate position toward said first end;
    wherein said second wall includes a cut-out region adjacent said first end to expose a portion of the surgical suture retainer, said cut-out region being enclosed by and sealed by said closure flap; and
    at least one suture having at least a portion thereof associated with said exposed portion of said surgical suture retainer.

12. A package according to claim 11, wherein said at least one suture includes a needle attached to each suture.

13. A package according to claim 11, wherein said cut-out region comprises a U-shaped tab die cut in said top wall.

14. A package according to claim 13, wherein said closure flap is secured to said second wall by said peripheral heat seal and at least one substantially transverse heat seal, said at least one transverse heat seal being secured to said U-shaped tab such that removal of said closure flap facilitates opening of said cut-out region to access said surgical suture retainer.

15. A package for surgical sutures according to claim 11, wherein said at least one suture is bioabsorbable.

16. A package for a surgical suture retainer comprising:
    a bottom wall of substantially moisture-impervious material forming a bottom of said package;
    a top wall of substantially moisture-impervious material forming a top of said package, said top wall having substantially the same dimensions as said bottom wall and being positioned in overlying relation to said bottom wall to form a pocket therebetween with a surgical suture retainer disposed in the pocket, said top wall being secured to said bottom wall by a substantially moisture-impervious peripheral seal, said top wall having a die-cut tab portion for accessing said surgical suture retainer;
    at least one suture associated with said surgical suture retainer such that at least a portion of a suture is positioned within said die-cut tab portion; and
    a closure flap of substantially moisture-impervious material overlying at least a portion of said top wall and enclosing said die-cut tab portion, said closure flap being secured to said top wall by a substantially moisture-impervious peelable peripheral seal, said closure flap terminating in a gripping tab portion positioned between first and second transverse edges of said top wall, whereby said package is opened in a single step by grasping said gripping tab portion and pulling said gripping tab portion towards said first transverse edge.

17. A package according to claim 16, wherein said die-cut tab portion comprises a U-shaped flap member.

18. A package according to claim 16, wherein said die-cut tab portion comprises a removal flap member.

19. A package according to claim 16, wherein said suture includes at least one needle attached to said suture.

20. A package according to claim 16, wherein said closure flap is secured to said top wall by said peripheral seal and at least one substantially transverse seal, said at least one transverse seal being secured to said die-cut tab portion such that removal of said closure flap facilitates exposure of said die-cut tab portion to access said surgical suture retainer.

21. A package for a surgical suture retainer according to claim 16, wherein said die cut tab portion is attached to said closure flap.

22. A method for packaging a surgical suture retainer, comprising the steps of:
    forming a bottom wall of substantially moisture-impervious material;
    forming a top wall of substantially moisture-impervious material having the same dimensions as said bottom wall;
    forming an access opening in said top wall;
    forming a closure flap of substantially moisture-impervious material having a gripping portion disposed at one end thereof;
    securing said closure flap to said top wall about a periphery of said closure flap to enclose said access opening such that said gripping portion is positioned between first and second transverse edges of said top wall;
    positioning a surgical suture retainer on said bottom wall, said surgical suture retainer including a plurality of sutures, such that at least a portion of said sutures are positioned beneath said access opening in said top wall; and
    securing said top wall having said closure flap thereon to said bottom wall about a periphery of said top and bottom walls to enclose said surgical suture retainer therein.

23. A method according to claim 22, wherein said step of forming an access opening in said top wall comprises die-cutting an aperture in said top wall.

24. A method according to claim 22, wherein said step of forming an access opening in said top wall comprises die-cutting a U-shaped tab in said top wall.

25. A method according to claim 24, further comprising the step of securing said closure flap to said top wall by a substantially transverse seal in addition to securing about said periphery, such that said closure flap is secured to said U-shaped tab.

26. A method according to claim 22, wherein said top wall is secured to said bottom wall by a peripheral heat weld seal.

27. A method according to claim 22, wherein said closure flap is secured to said top wall by a peripheral peelable heat seal.

28. A method according to claim 22, wherein each suture of said plurality of sutures includes a needle attached thereto.

29. A package for a surgical suture retainer comprising:
    a wall of substantially moisture-impervious material forming a bottom of said package.
    a wall of substantially moisture-impervious material forming a top of said package, said top wall having substantially the same dimensions as said bottom wall and being positioned in overlying relation on said bottom wall to form a pocket therebetween for receiving a surgical suture retainer, said top wall being secured to said bottom wall by a substantially moisture-impervious peripheral seal;
    an access opening formed in said top wall for accessing at least a portion of said surgical suture retainer therethrough;
    a closure flap of substantially moisture-impervious material enclosing said die-cut portion, said closure flap being secured to said top wall by a substantially moisture-impervious peelable peripheral seal, said closure flap terminating in a gripping tab portion positioned between first and second transverse edges of said top wall, whereby said package is opened in a single step by grasping said gripping tab portion and pulling said gripping tab portion towards said first transverse edge; and
    at least one suture-needle assembly, having a needle member positioned for accessing said suture-needle assembly within said access opening.

30. A package for a surgical suture retainer according to claim 28 wherein said access opening is a die-cut portion.

31. A package for a surgical suture retainer according to claim 28 wherein said access opening is a window.

32. A package for a surgical suture-needle assembly comprising:
    a wall of substantially moisture-impervious material forming a bottom of said package,
    a wall of substantially moisture-impervious material forming a top of said package, said top wall having substantially the same dimensions as said bottom wall and being positioned in overlying relation on said bottom wall to form a pocket therebetween for receiving a surgical suture retainer, said top wall being secured to said bottom wall by a substantially moisture-impervious peripheral seal, said top wall having an access region formed therein;
    a surgical suture retainer disposed between said top and bottom walls with at least a portion of said surgical suture retainer disposed adjacent said access region;
    a closure flap of substantially moisture-impervious material enclosing said access region, said closure flap being secured to said top wall by a substantially moisture-impervious peelable peripheral seal, said closure flap terminating in a gripping tab portion positioned between first and second transverse edges of said top wall, whereby said package is opened in a single step by grasping said gripping tab portion and pulling said gripping tab portion towards said first transverse edge; and
    at least one suture-needle assembly associated with said surgical suture retainer and having a needle positioned for accessing said suture-needle assembly through said access region.

* * * * *